(12) United States Patent
Gual Pasalodos

(10) Patent No.: US 9,468,949 B2
(45) Date of Patent: Oct. 18, 2016

(54) AUTOMATIC DEVICE FOR SEPARATING PRODUCTS ACCORDING TO EXTERNAL DEFECTS, AND METHOD FOR RELEASING SAID PRODUCTS

(71) Applicant: CITRODIAGNOSIS SELECTIVA, S.L., Albuixech (ES)

(72) Inventor: Mariano Gual Pasalodos, Valencia (ES)

(73) Assignee: CITRODIAGNOSIS SELECTIVA, S.L., Albuixech (Valencia) (ES)

( * ) Notice: Subject to any disclaimer, the term of this patent is extended or adjusted under 35 U.S.C. 154(b) by 0 days.

(21) Appl. No.: 14/441,566

(22) PCT Filed: Nov. 14, 2013

(86) PCT No.: PCT/ES2013/070797
§ 371 (c)(1),
(2) Date: May 8, 2015

(87) PCT Pub. No.: WO2014/076345
PCT Pub. Date: May 22, 2014

(65) Prior Publication Data
US 2015/0306635 A1    Oct. 29, 2015

(30) Foreign Application Priority Data
Nov. 16, 2012   (ES) .................................. 201201171

(51) Int. Cl.
*B07C 5/36* (2006.01)
*B65G 47/86* (2006.01)
(Continued)

(52) U.S. Cl.
CPC ................. *B07C 5/362* (2013.01); *B07C 5/34* (2013.01); *B07C 5/342* (2013.01); *B07C 5/3422* (2013.01); *B07C 5/36* (2013.01); *B65G 17/24* (2013.01); *B65G 47/24* (2013.01); *B65G 47/842* (2013.01); *G01N 21/8806* (2013.01); *G01N 21/8851* (2013.01); *G01N 21/951* (2013.01);
(Continued)

(58) Field of Classification Search
CPC ... B07C 5/36; B07C 2501/009; B65G 17/12; B65G 17/14; B65G 47/86; B65G 47/90; B65G 47/842; B65G 2201/0211; B65G 2812/02603; B65G 2812/02663; B65G 2812/02712
See application file for complete search history.

(56) References Cited

U.S. PATENT DOCUMENTS 2,927,680 A * 3/1960 Shappell ................ B65G 47/00
                                                    198/502.2
2,969,867 A * 1/1961 McClelland ............. A23N 4/04
                                                       198/385

(Continued)

FOREIGN PATENT DOCUMENTS

ES    2155109    12/1995
ES    2282188     3/2002
(Continued)

*Primary Examiner* — Joseph C Rodriguez
(74) *Attorney, Agent, or Firm* — Richard M. Goldberg

(57) ABSTRACT

An automatic device for separating products based on their external flaws, includes a mechanism for selective separation and discharge of the products, in which the suitable products are unloaded onto a first discharge conveyor, and the unsuitable products are unloaded onto a second discharge conveyor; and a set of securing clamps for the products in their radial displacement on the discharge head of the machine jointly and simultaneously with the transport items of the products, whose activation depends on the suitable or unsuitable status of the product.

13 Claims, 8 Drawing Sheets

(51) Int. Cl.
  *B07C 5/34* (2006.01)
  *B07C 5/342* (2006.01)
  *B65G 17/24* (2006.01)
  *B65G 47/24* (2006.01)
  *G01N 21/88* (2006.01)
  *G01N 21/95* (2006.01)
  *G01N 21/84* (2006.01)

(52) U.S. Cl.
  CPC ... *B07C2501/009* (2013.01); *G01N 2021/845* (2013.01); *G01N 2021/8466* (2013.01); *G01N 2021/8854* (2013.01)

(56) References Cited

U.S. PATENT DOCUMENTS

| | | | | |
|---|---|---|---|---|
| 3,300,027 A * | 1/1967 | Booij | ............. | B65B 5/101 198/704 |
| 3,837,474 A * | 9/1974 | Brooke | ............. | B65B 35/36 198/374 |
| 3,915,315 A * | 10/1975 | Miller | ............. | B21B 39/32 271/903 |
| 3,944,047 A * | 3/1976 | Mumma | ............. | B65G 47/846 198/370.08 |
| 4,775,051 A * | 10/1988 | van der Schoot | ...... | B07C 5/361 198/369.1 |
| 5,030,001 A * | 7/1991 | vande Vis | ............. | G01N 33/085 209/510 |
| 5,749,453 A * | 5/1998 | Doornekamp | ......... | B65B 23/06 198/377.03 |
| 5,865,291 A | 2/1999 | Affeldt et al. | | |
| 6,234,300 B1 * | 5/2001 | De Vos | ............. | B07C 5/18 198/370.03 |
| 6,311,848 B1 * | 11/2001 | Zenzerovich | ......... | B65G 47/962 198/370.01 |
| 6,446,784 B1 * | 9/2002 | Veldhuizen | ............. | B65B 23/08 198/394 |
| 6,742,647 B2 * | 6/2004 | De Greef | ............. | B65G 17/323 198/470.1 |
| 7,185,753 B2 * | 3/2007 | Hartness | ............. | B65G 17/323 198/474.1 |
| 7,207,434 B2 * | 4/2007 | Hartness | ............. | B65G 17/323 198/468.2 |
| 7,622,691 B2 * | 11/2009 | De Greef | ............. | B07C 5/36 209/576 |
| 9,199,795 B2 * | 12/2015 | Bliss | ............. | B65B 23/08 |
| 2009/0000909 A1 * | 1/2009 | Hollriegl | ............. | B65G 47/842 198/377.03 |
| 2015/0259145 A1 * | 9/2015 | Fenile | ............. | B65G 17/12 198/803.3 |

FOREIGN PATENT DOCUMENTS

WO   2011/154017 A1   12/2011
WO   2012/038576 A1    3/2012

* cited by examiner

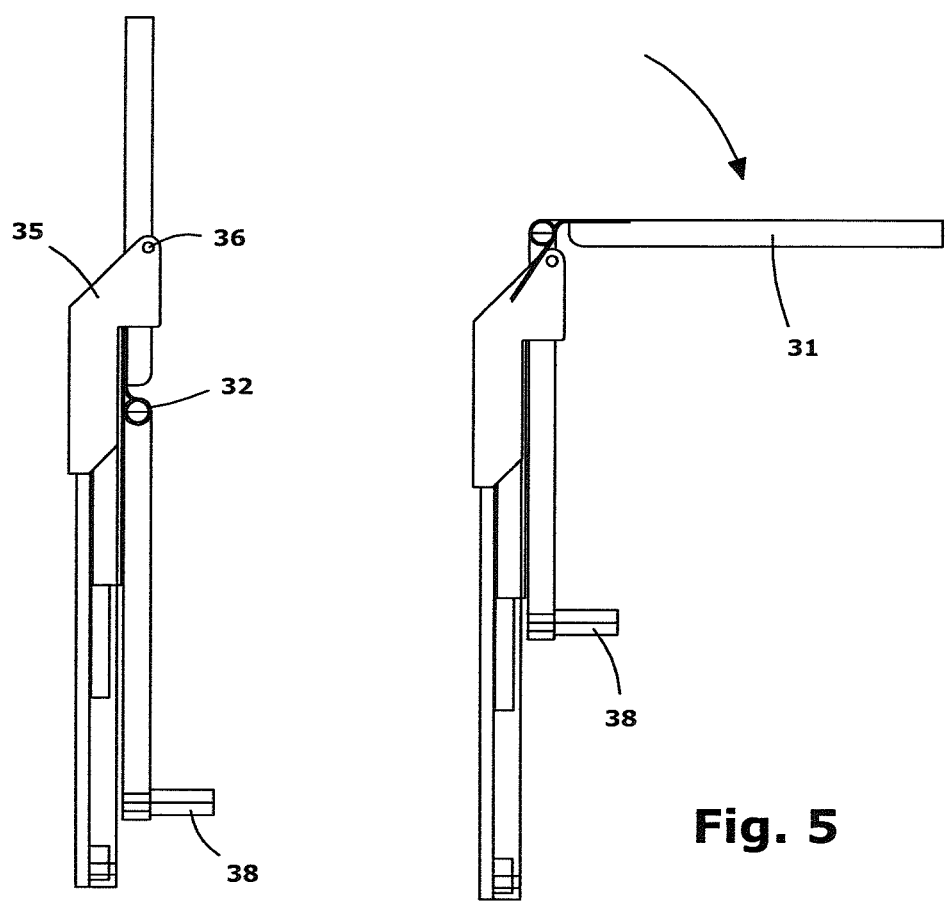

AUTOMATIC DEVICE FOR SEPARATING PRODUCTS ACCORDING TO EXTERNAL DEFECTS, AND METHOD FOR RELEASING SAID PRODUCTS

An automatic device for separating products on the basis of their external flaws, and a procedure for discharging these products.

This invention covers a device for individualised separation of products, particularly fruit, and more particularly citrus fruit, depending on whether they are considered suitable or not in an automatic system complementary to, but lying outside the scope of this invention, so that the suitable fruit goes to a packaging zone and the rejected fruit goes to a zone for rejects or selection for other purposes, such as its use for juice, etc.

The device being described herein is made up of the end of a fruit conveyor system in the form of a set of modular chains which hold axles in turn holding supporting pads, which individually move the fruit along the inspection zone, and unload this at its end, which must obviously be done at the same speed as the inspection and feeding. With the invention being proposed the fruit can respectively be discharged in real time to a zone for receiving suitable fruit or a zone for unsuitable fruit.

The purpose as a whole of this invention is thus to provide fruit and vegetable packing plants with an automatic and effective system for removing rotten items (fruit infested by fungi which must as a priority be got away from other sound fruit in the post-harvest stage, as this affects the fruit around it by contact).

The distribution device being proposed is ideal for being located at the outlet of an automatic detection system as part of a fruit processing plant, forming an assembly to be placed after the general sorting stage, in order to replace today's "discotheques" or manual selection booths, and before the application of waxes, but after prior selecting, washing and drying of fruit for proper viewing with the least possible dirt.

BACKGROUND OF THE INVENTION

At the present time there are fruit transport systems for its discrimination and later size-grading integrated as components of electronic sizers able to differentiate fruit and scan its surface, in order to evaluate this according to quality parameters by optical selection of defects. Later on its equatorial diameter, weight and volume are calibrated and this is distributed by conveyors integrated in the sizer which send the fruit calibrated in this way to different zones for preparing and packing the product, by means of guide plates, selection hatches, jettison devices, amongst others. In the first of these cases two outlet conveyors are needed for each inlet conveyor, which requires an increase in the width, always unwanted and often not feasible through the spaces in this kind of installations being optimised. In the others, as the fruit falls by gravity, this causes an impact on at least one part of the fruit, either the suitable or the unsuitable fruit, which will in many cases make this burst and leave juice on the transport items.

The installation of the electronic type of sizer requires linear distribution of its structure and distribution conveyors perpendicular to this, spread over its whole length at minimum distances from each other, which entails major demands as regards the size of machinery and thus great expense and long payback periods as compared with conventional central sizing machines with tilting rollers.

In electronic sizing for the fruit and vegetable products as mentioned above, systems for transporting and differentiating fruit for its sizing and later distribution are used with similar technical solutions in most of the sizers currently available on the market.

The intention is nevertheless to prevent battering the fruit by means of a gentle selection at the unloading point at different heights.

The system used consists of a group of conveyors known as singulators, forming a set of parallel tracks, arranged in groups of two, and constituting a V shape, forming an angle of roughly 90°. The fruit from the processing line is transported one by one on these singulating conveyors. The dimensions of this first assembly depend on the production and manufacturer's requirements, usually being about five meters long.

After the singulator conveyors mentioned, there is a following module known as a differentiator, which is synchronised with the singulator conveyors. This is a set of chains which support twin cone or bobbin rollers (diabolos) on the sides, mounted in sets of two on their respective axles along their entire length.

SUMMARY OF THE INVENTION

The invention being proposed consists of an automatic selector for distribution of fresh fruit on the processing line depending on the information obtained from an artificial vision device located in a selection unit, where a fruit is determined to be suitable or not, as this fruit goes through said unit.

After completing its travel through the unit, depending on whether the system has determined if the fruit is suitable or not, the fruit is made to unload through gravity on a sloping ramp, or held by securing clamps until it reaches a lower discharge position.

The system is made up of a set of tracks comprising two or more chains which pull along hemispheres made of rubber of some other similar foodstuff-quality material which hold and come into direct contact with the fruit, which will from this point be known as 'supporting pads'. These hemispheres are mounted on the modular chains facing each other, so that each pair of these and the following or previous pair form a nest which cradles each piece of fruit.

Hence, according to the invention, this describes a device for retaining the rejected fruit in the display and classification stage, so that this prevents it from going on to the general processing line for suitable products. The mechanism is fitted on the drive head of the machine, and holds the fruit to be rejected by its top, keeping this secured throughout the rotation of the head until the fruit reaches the lower part of the chain in a different zone to where the sound fruit drops through gravity.

This difference in the place where the fruit is collected enables separating and accurately leading one sort away from the other. While the sound fruit continues to advance in its processing on the line by its frontal unloading by gravity onto the following collection conveyor, the flawed fruit is "forced" to follow the path of the supporting pads on the modular chain to then be discharged at its bottom.

This system gives the assembly great advantages in respect of the current systems for lateral discharge on a lower collection conveyor used in the big electronic calibration machines, by minimising the width of the machine and enabling this to be integrated on standard processing lines of fruit and vegetable packing plants.

The assembly is more specifically made up of a steel frame holding the items described below.

A drive system of at least one drag chain; in one material embodiment, the chain is a commercially available chain of the sort with hollow-pin steel slats and with a pitch of roughly ¾ inch; every certain number of slats of the chain, normally every two, this holds and moves an axle, and this axle in turn holds at least a pair of supporting pads; the pads are made of a high-friction foodstuff-quality material suitable for contact with fruit.

Each pair of supporting pads is mounted on said axle, which is in turn secured to the chain through the hollow pins of its shaft journals, so as to allow some relative movement between the chain and said axle. The supporting pads are in turn fitted on the chain facing each other in sets of two, so that a housing is created between each four supporting pads which cradles the fruit and controls its rotation and transfer, as will be seen below. This means that the movement of the axles holding the supporting pads goes along with the movement of the parts of the chain. The supporting pads are also fitted on the carrying axles in such a way that the relative rotation between axle and supporting pad is free and independent for each supporting pad.

The frame can be modular, and preferably, in this case, the motor parts and some of the drive elements, particularly the chains, can be shared by the adjacent module, so that one item of the chain holds the axle carrying the supporting pads on both one side and the other, thus avoiding any unnecessary components.

The assembly has one drive/take-up head and another free head for facilitating dropping the fruit in its unloading at the front, in its integration in the corresponding processing line.

The fruit is fed in at the rear of the machine (the inlet) and converges in the nests created by each set of four supporting pads so that only one piece of fruit fits in each of these.

Since the supporting pads are held on axles joined to the elements of the chain, the chain's movement means that the supporting pads move in turn, thus carrying along the fruit housed in these.

The discharge is done in such a way that there are clamps, synchronised with the travel of the supporting pad housings, that can be in two positions at the discharge head. These positions are:
- a withdrawn position, in which they do not hold the fruit, when the system indicates that the fruit is suitable, and
- an extended position, in which the fruit is secured and forced to follow the rotation of the supporting pads to a lower discharge position for the rejected fruit.

The extended and withdrawn positions are provided by a dual cam profile, variable depending on the operation status of a tab or pawl which will be determined by the suitable/unsuitable status of the fruit in the relevant position. The cam profile follower is in each of the clamp members.

BRIEF DESCRIPTION OF THE DRAWINGS

In order to illustrate the invention being described, we are adjoining eleven sheets of drawings to this report, in which fourteen figures represent the essence of this invention, as an example without constituting any limitation thereto, and in which:

FIG. 4 shows a schematic side view of the assembly of FIG. 2;

FIG. 5 shows a schematic side view of the assembly of FIG. 3;

Figure 1:
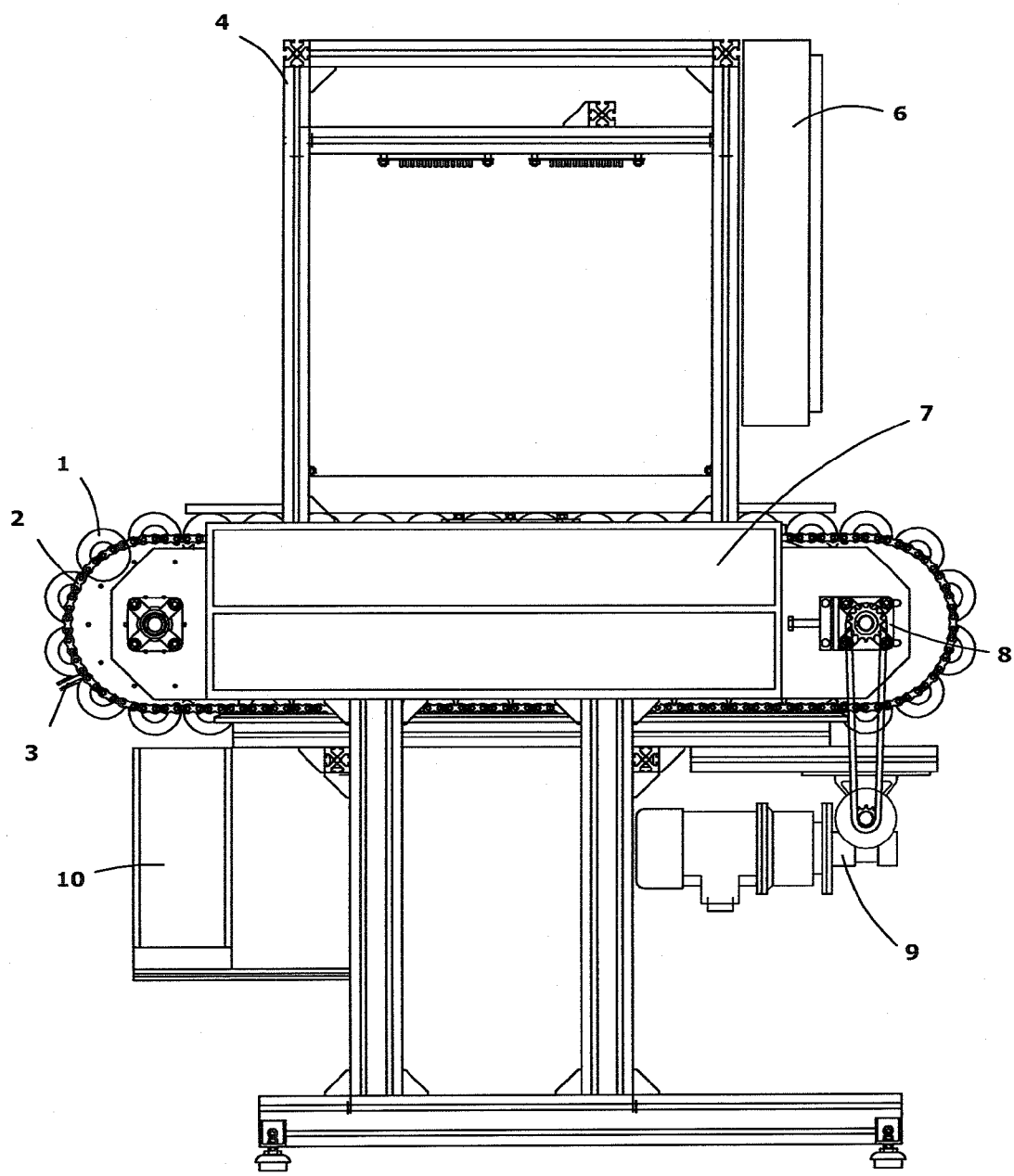
FIG. 1 shows a general side view of the machine of the invention.
Figure 2:
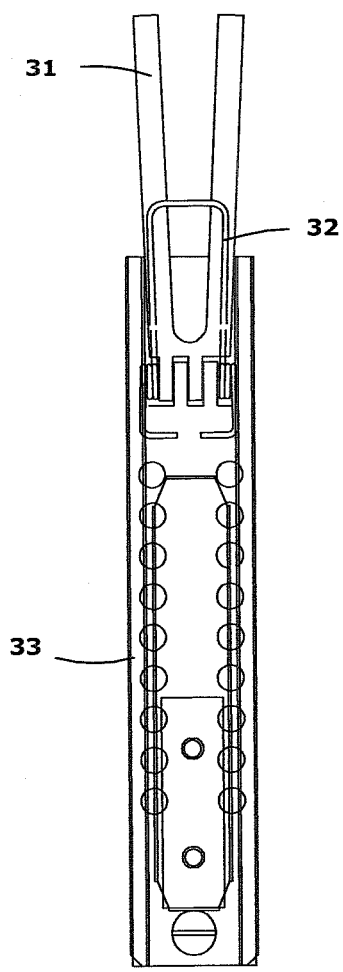
FIG. 2 shows a schematic front view of an assembly for retaining fruit in transit, for its discharge from the main line, in withdrawn position.
Figure 3:
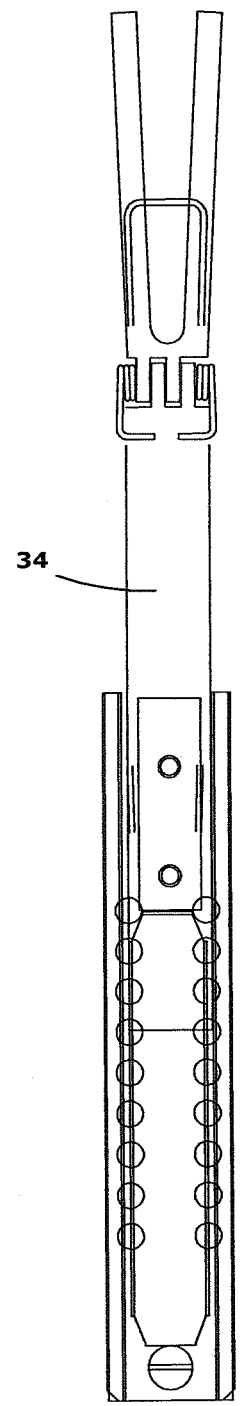
FIG. 3 shows a schematic front view of an assembly for retaining fruit of FIG. 2, in extended position.
Figure 6:
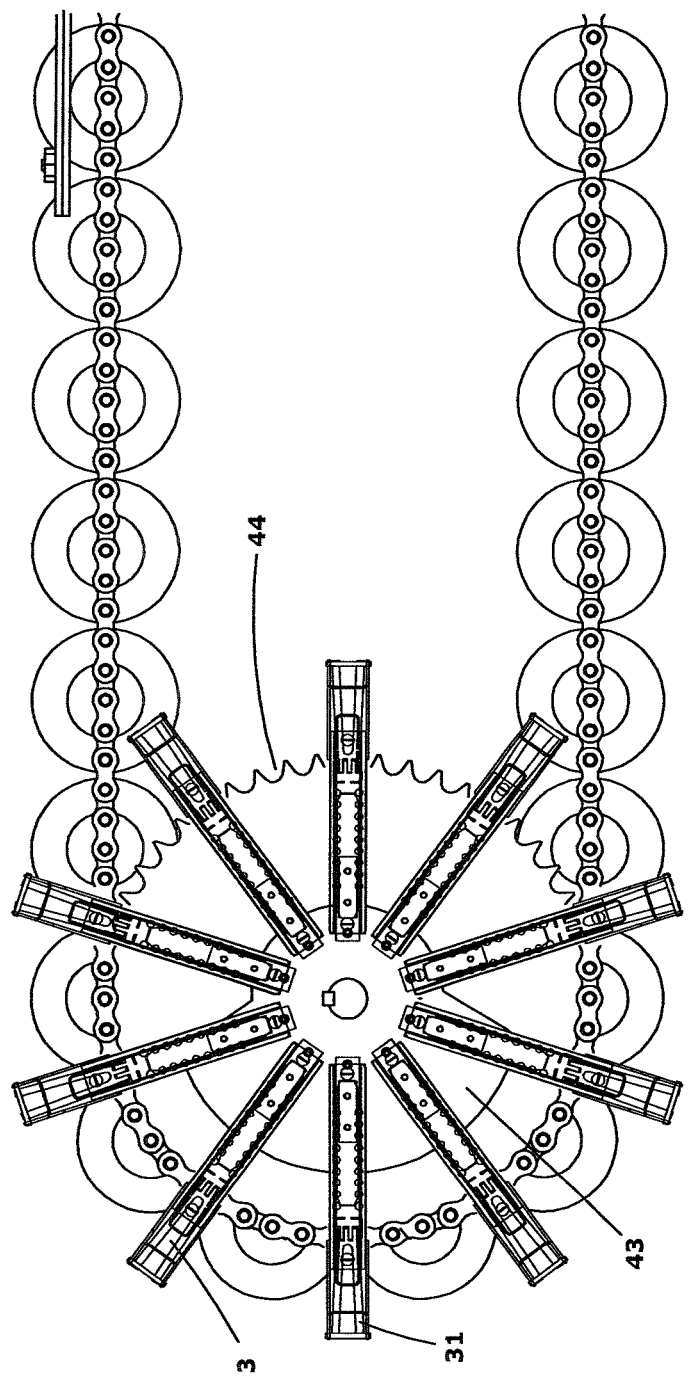
FIG. 6 shows a schematic side view of one end of the machine of the invention fitted with a set of retaining assemblies of FIGS. 2 to 5.
Figure 7:
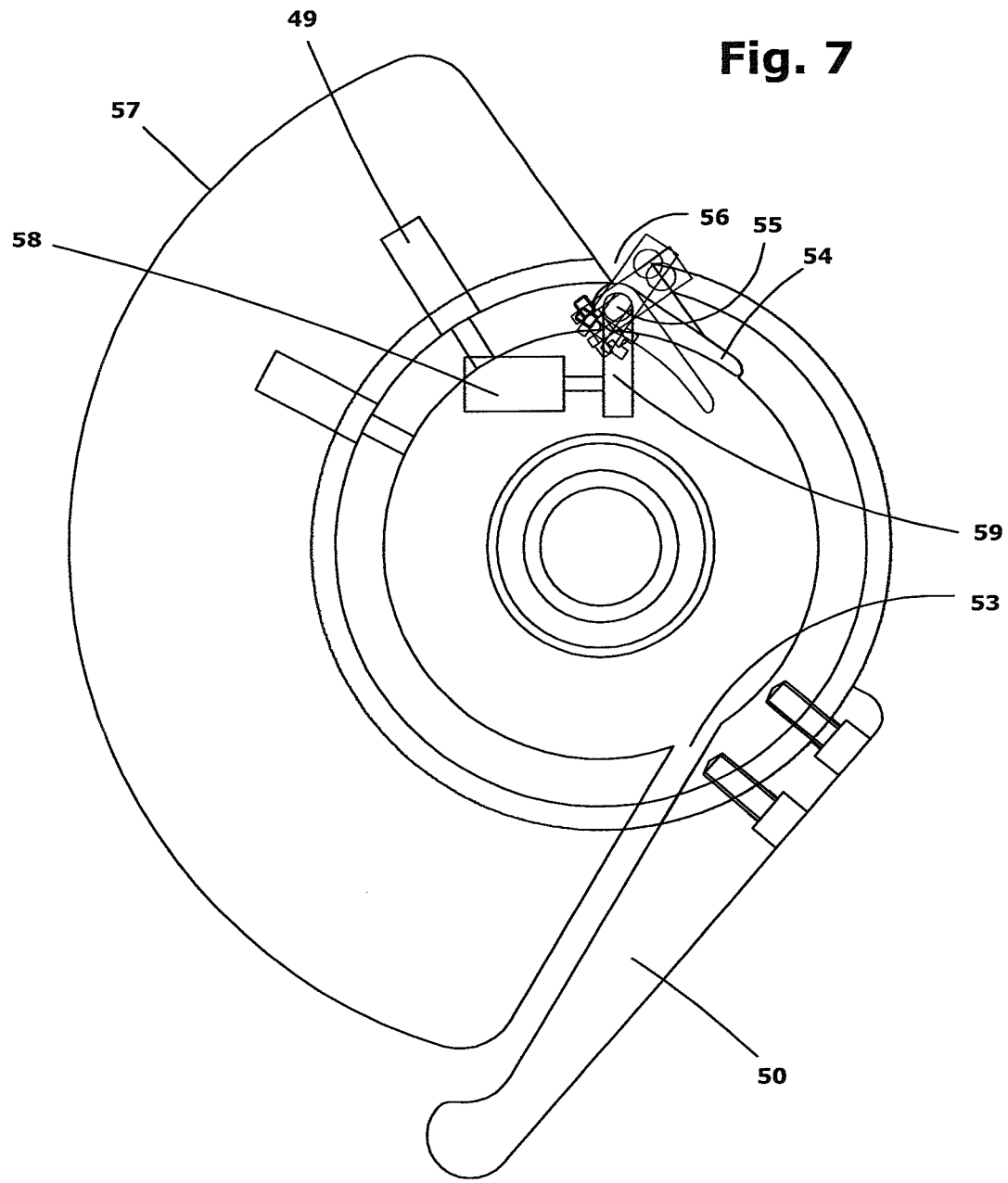
FIG. 7 shows a schematic side view of the fruit selector distributor.

These figures show the following references:
1 Support pads
2 Transport chains
3 Mechanism for retaining rejected fruit; this is integrated in the front head of the machine
4 Upper frame; this is modular and surrounds the systems for lighting and artificial vision
6 Electric and electronic control panel
7 Main frame: this is modular, and is normally made of aluminium, steel or some other material for supporting bodies and adapted for its lateral extension
8 Drive/take up head for the drag chains
9 Motor—electronic drive
10 Conveyor for removing the fruit rejected by the system
31 Holding clamps for the retaining element
32 Spring of the retaining element
33 Extraction guide of the retaining element
34 Extractable body of the retaining element
35 Protector of the spring 32 and of the holding clamps 31
36 Spring back-pressure pin 32
38 Extractable body lug
43 Distributor of the holding clamps
44 Front pinion for pulling the drive chain of the hemispheres
49 Position sensors
50 Lower arm
53 Guide groove for re-entry of the lugs
54 Guide pawl
55 Pawl pin
56 Upper groove of the lug outlet 38
57 Outer cam profile for sliding of the lugs 38
58 Electromagnet
59 Operating arm of the pawl 54
63 Interior travel of the lugs 38
66 Outer travel of the lugs 38
71 Retained fruit
73 Unretained fruit
74 Unloaded fruit
78 Conveyor for collecting sound fruit

PREFERENTIAL EMBODIMENT OF THE INVENTION

The purpose of this invention is an automatic device for separating spheroidal products depending on their flaws, in accordance with the information provided by a computer system according to an evaluation previously carried out, normally in part of the machine itself. These products will normally be fruit, particularly citrus fruit.

It is thus necessary to ensure the processing of a large amount of fresh spheroidal fruit and to handle this with great accuracy, speed and efficiency, as part of a processing installation for fruit and vegetable produce in which any breakdown or performance reduction of any of its components entails enormous damages. In accordance with a particular embodiment, the machine is made on a solid, compact frame which surrounds and holds the different parts of the system. This obviously has to adapt to the fruit infeed and outfeed heights required by the installation. For height adjustment of the items the frame is designed to incorporate legs with adjustable height supports.

According to one embodiment, the frame (4, 7) is made of assembled structural aluminium profiles to hold the items, or made of stainless steel plate for protection of the industrial environment in which this is located.

The machine of the invention is modular, meaning that the installation can "grow" or adapt to installations of any size by adding modules in parallel, being able to share some common items, such as systems for control or drive items.

A two-line module is described as an example of the embodiment, as this is considered to be the most appropriate for later expansion. The machine thus houses two lines of modular chains comprising two sets of support pads (1) arranged in parallel, which house the fruit in successive pairs; the machine can nevertheless be made up of a single line (one set of support pads) or by more than two lines, these lines or sets of support pads being able to be arranged in parallel as independent units or sharing mechanical items.

In this example of an embodiment, as shown in FIG. 1, the machine is made up of a main frame (7), which holds two heads, one a drive/take-up head (8) with its motor (9) located at one end of the machine, and another frontal freely-rotating head located at the other end of the machine, where there is a retention mechanism (3) for discriminated fruit. The two heads comprise their own pinions or sets of pinions (44) which pull two drag chains (2). These chains (2) are made up of elements, and every certain number of elements the corresponding element holds an axle carrying the support pads which in turn hold the fruit. According to a particular embodiment, the chain is made up of elements of roughly % inch. The axles held by the chains house pairs of supporting pads (1), at regular distances. According to the two-line embodiment described, each axle will house two parts of supporting pads and will be pulled by one or more chains. Each line could nevertheless have independent axles from those of the other line. According to the example of an embodiment, the axles carrying the supporting pads (1) are pulled by three chains. The supporting pads (1) are made up of hemispheres or truncated cones with varying profile, converging towards the centre of the pair which these form; each two pairs of successive supporting pads (1) form a housing for one piece of fruit. The supporting pads are for example made of rubber, or any other foodstuff-quality, rough material; their sizes will be as appropriate for the fruit to be treated, and they will be arranged a regular intervals, for example, every two elements of the chain. At least the top of the chain travel is protected by a chain cover, which prevents contact with the fruit and facilitates its maintenance.

According to information obtained during the processing of the fruit, it is determined whether the fruit is in suitable condition to be packed and marketed or whether it has to be rejected through being unsuitable, for example, to be sent for a new selection of lower qualities and/or for other uses, such as juices.

As has been stated, the machine comprises a system for extraction of the rejected fruit. This extraction system comprises a retaining mechanism (3) for each nest made up of two successive pairs of support pads, with a set of items for retaining the fruit, in the form of a two-way travel cam profile, which will be activated when the control system (6) determines that the fruit is not suitable. The retention mechanism is rotatory along with the rotation of the chain on the discharge head.

Figure 10:
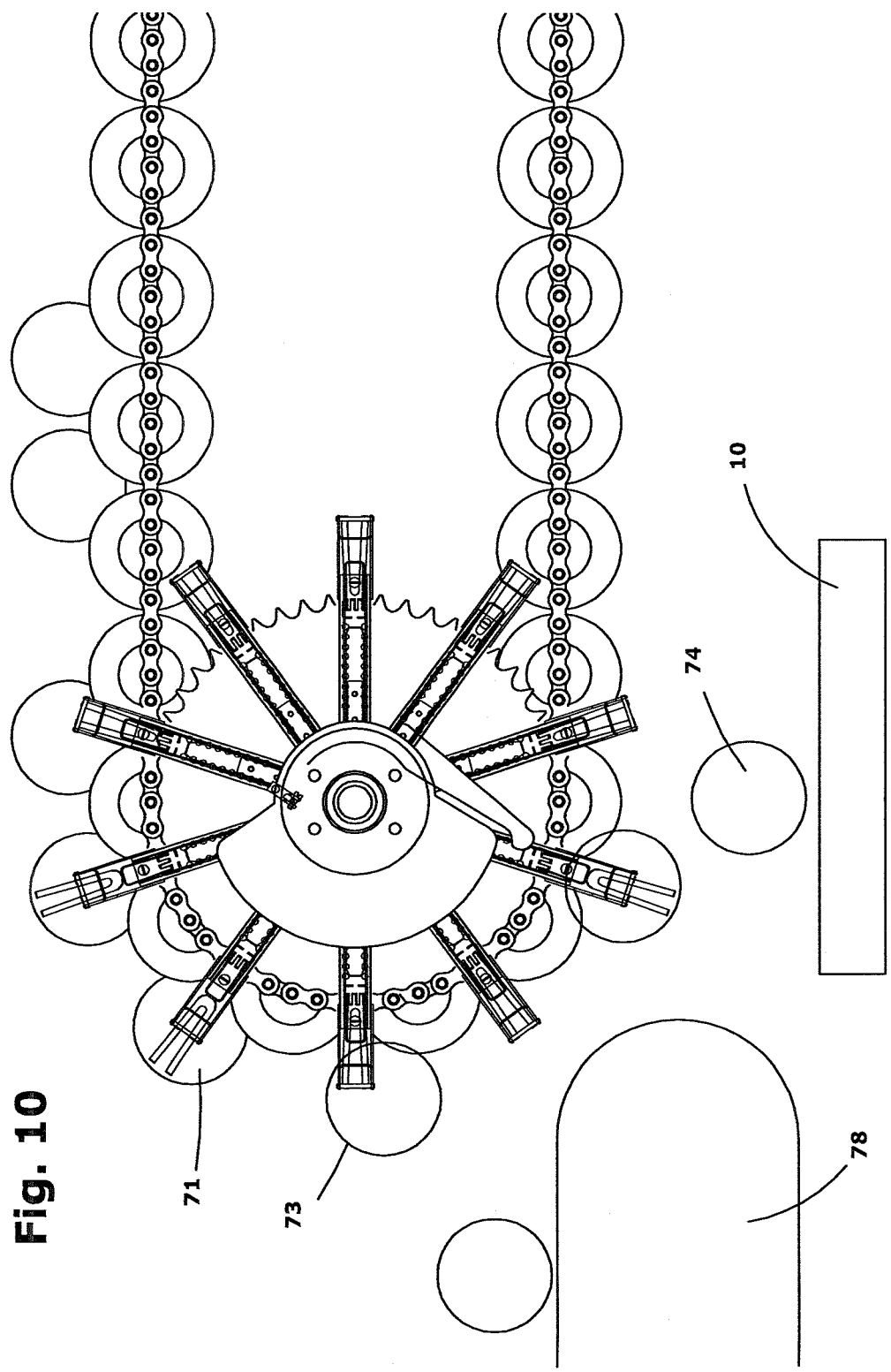
FIG. 10 shows a schematic lateral view of the machine in which one can appreciate the discrimination of the fruit depending on the status of the retaining elements.

As can be seen in the example of the embodiment of FIG. 10, ten independent extractors have been mounted on the drive pinion of the chain so that these coincide with the hollows forming the housings defined by the support pads. Their distribution is radial, so that they turn along with the pinion as regards their position and speed.

Each of the retaining items comprises a fixed body which forms an extraction guide (33) of at least one set of holding clamps (31) for the fruit (this can be one clamp on each side); these retaining elements move along with the pinion and comprise an extractable body (34), which in turn comprises the retaining element, the holding clamps (31). The extractable body (34) comprises a lug (38) which follows a cam profile; the cam profile has a dual travel determined by the action of the guide pawl (54) as will be seen below. The travel of the lug along one of the routes makes the clamps extract, while in the other they remain inactive (retracted).

The holding clamps (31) of the retaining element are hinged to the extractable body (34), and forced into a sloping position through the action of a spring (32), which acts by support on a back pressure axle (36). A protective element (35) for the spring (32) and the holding clamps (31) is designed. The clamps comprise parallel elongated items in the shape of a finger which press the fruit against the supporting pads.

The actuator of the retaining items is made up of the distributor of the holding clamps (43) which comprises a dual circuit cam profile, so that when the fruit is suitable, the route taken by the actuators of the retaining elements is circular (interior), without there being any retention. When the unsuitable signal is received, however, the system activates a pawl which forces the actuator of the retaining element to go along a second circuit, where the holding clamps (31) and retainers are operated. The set of mechanisms is fitted on the axle of the front pinion (44) for pulling the chain at the front head of the machine, but the distributor of the holding clamps is in a fixed position.

Figure 8:
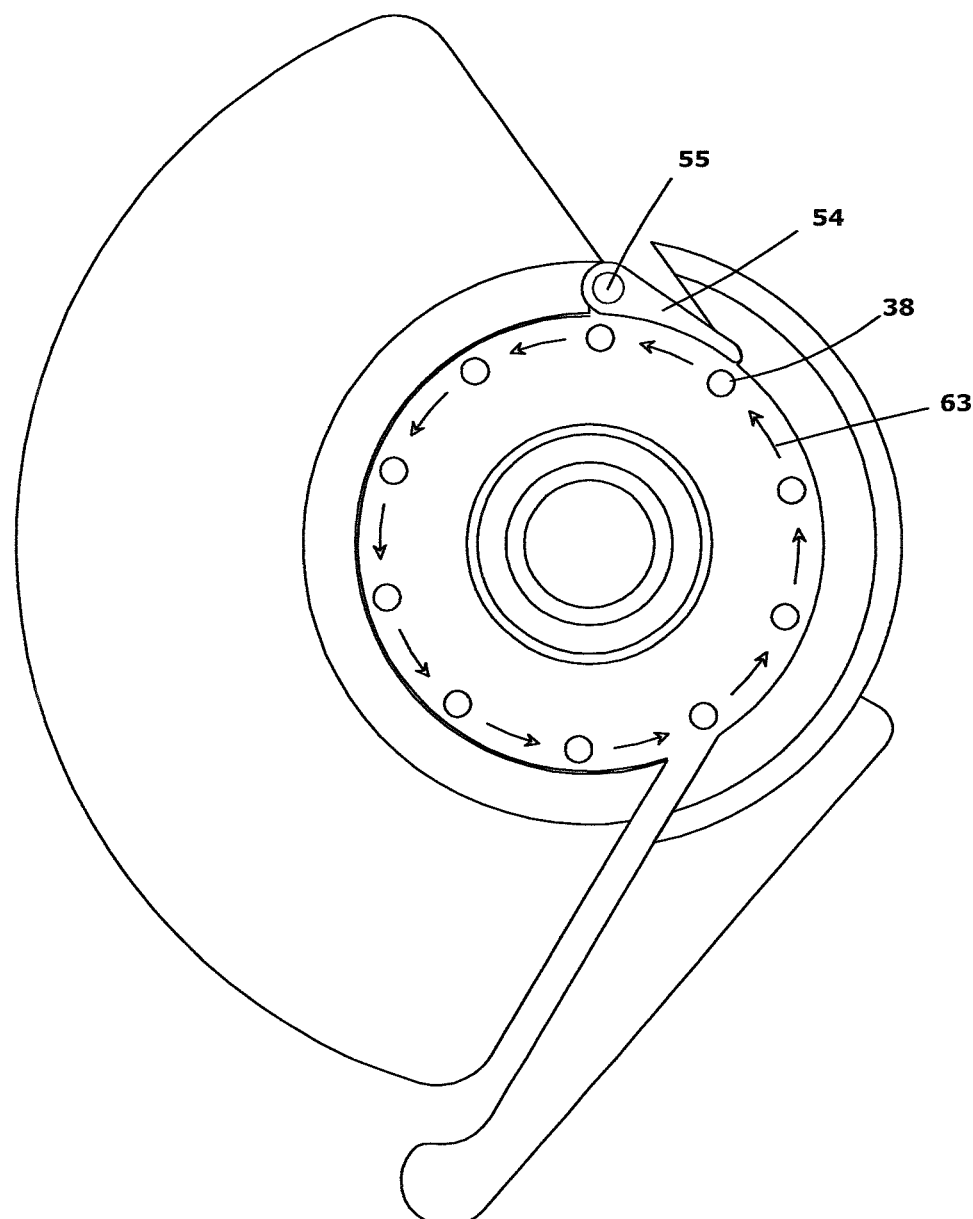
FIG. 8 shows a schematic view of the travel of the lugs in the distributor when no fruit is to be separated, with the separation device in passive position.
Figure 9:
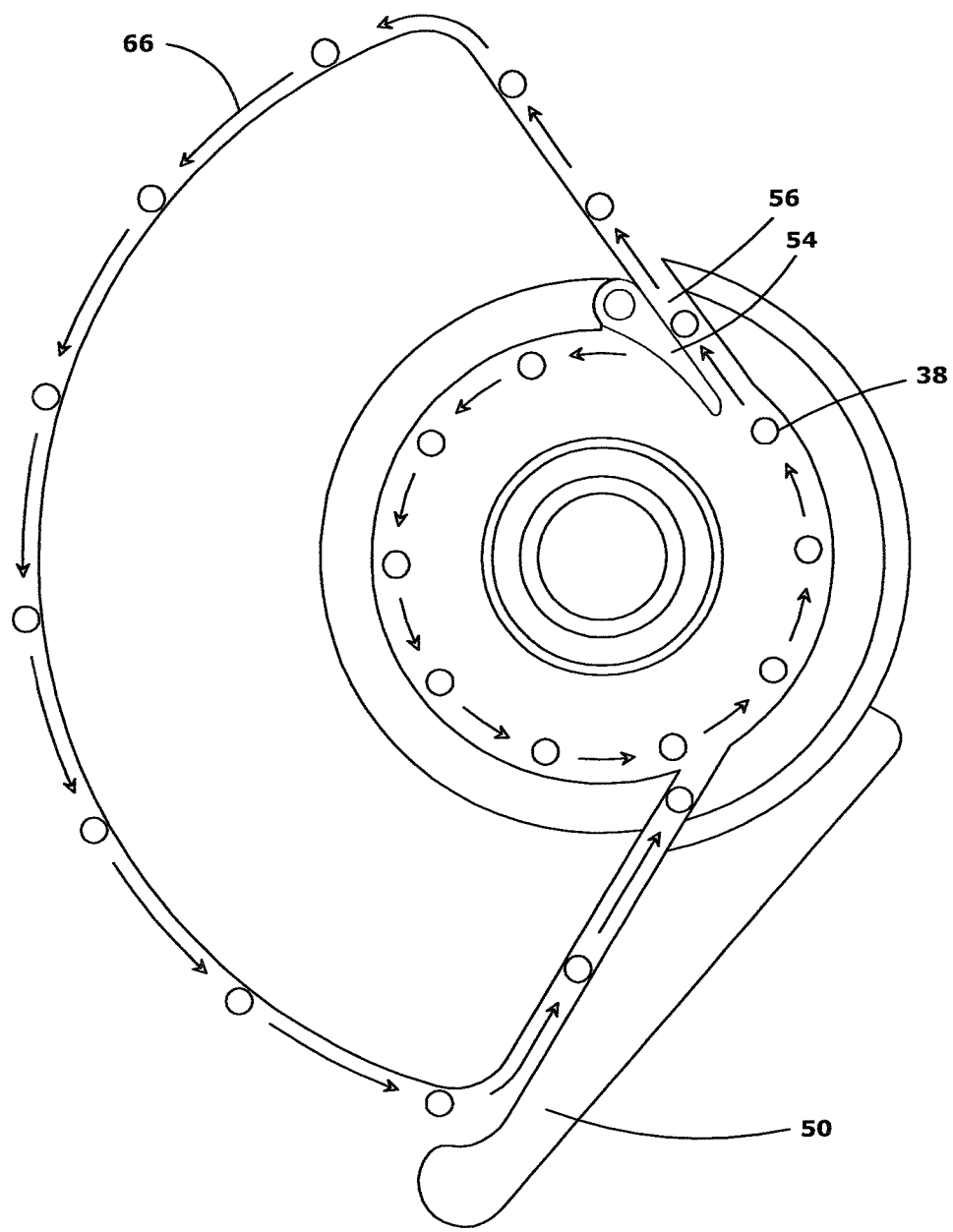
FIG. 9 shows a schematic view of the travel of the lugs in the distributor when a fruit has to be separated, with the separation device in active position.

In FIGS. 8 and 9 the route taken by the lugs (38) of the retaining items in the cam profile can be seen. FIG. 8 shows the route taken by a lug in different positions, when the corresponding fruit is suitable, when there is no radial displacement of the lug. The guide pawl (54) hinged at the axle (55) is in a first closed position, idle, in which the lug is forced to follow the interior route. (63) shows the travel of the lug (38), with no radial displacement. FIG. 9 shows the route taken by a lug (38) of a retainer element on the cam profile, in which after receiving the order from the control system through having detected unsuitable conditions, the guide pawl (54) goes into its open position, forcing the lug to follow the outer cam profile (57) along outer path (66). Since there is radial displacement of the lug (38), this causes the extraction of the extractable body (34) of the retaining element, and the fruit is "clasped" by these clamps through the spring (32), for which reason the fruit will not be unloaded by gravity in the dropping position, but will carry on turning in its housing until it reaches the position of a discharge conveyor (10). As the pawl opens, the lug (38) is forced to enter the upper outlet groove (56), to follow the outer cam profile (57) and to return to the idle or retracted position through the guide groove (53) determined by the stop on the lower arm (50). The guide pawl (54) is opened by means of an electromagnet (58) or an electric actuator, which moves a drive arm (59), and this in turn moves the guide pawl (54).

The distributor is placed on a plane parallel to the drive pinion of the chain, held to the main axle by means of a ball bearing. The guide pawl (54) will be activated in one position or another for each lug (38) that goes by.

Position sensors (49) (photocells or inductive position sensors) will determine the position of the lugs, and ascertain whether these have already gone by the cam or not. Hence, by means of the joint action of the position sensors (49) and the guide pawl (54) the retaining systems are accurately and promptly diverted towards the route for capturing the fruit indicated by the system.

The lugs (38) are normally screwed to the extractable body of the retainer assembly.

As can be seen in FIG. 10, when a fruit reaches the outlet head, it can be freely housed in the support pad housing, without being retained (73) when this does not have to be rejected, for which reason it falls through gravity onto a conveyor for fruit without flaws (78), which leads this to a later process in the treatment line. On the other hand, when the fruit has to be rejected, it is retained (71) by the clamps (31), and will thus not fall, being held to the head. The clamps are only retracted when the lugs (38) of the retainer items return to the inner position of the cam, thus releasing the fruit (74), which will fall onto a conveyor for removing rejected fruit (10).

Finally the invention also refers to a procedure for discharging fruit, which comprises unloading this by free fall onto a conveyor for collecting accepted fruit, and securing the rejected items by means of holding clamps to prevent this free fall, so that this is only released by said clamps, which act following a cam profile, when they reach the position of a conveyor for discharge of rejected fruit, normally placed in a lower position.

The invention claimed is:

1. An automatic device for separating products on the basis of detected external flaws thereof, that are adapted to be integrated in a processing line of a machine in a fruit processing and packaging plant, the device comprising:
   transport elements which transport the products, the transport elements being formed of a set of supporting pads, in which each two successive pairs of supporting pads determine a housing for one said product, and
   a mechanism for selective separation and discharge of the products from the transport elements, in which suitable ones of the products are removed onto a first discharge conveyor, and unsuitable, flawed ones of the products are removed onto a second discharge conveyor, the mechanism including a set of retainer elements for radially displacing the products on the first discharge conveyor or the second discharge conveyor in synchronism with movement of the transport elements for the products, upon activation thereof in dependence on a suitable or unsuitable status of the product, the retainer elements movable between:
      a first position that permits products which are not flawed to be displaced radially to the first discharge conveyor and
      a second position at which the retainer elements support and clamp flawed ones of the products to the transport elements for carrying the flawed ones of the products to a position corresponding to the second discharge conveyor.

2. The device, according to claim 1, wherein the transport elements include said supporting pads in the form of one of hemispheres and truncated cones with variable sections.

3. The device, according to claim 2, wherein the supporting pads are made of a rough, foodstuff-quality material.

4. The device, according to claim 1, wherein the first discharge conveyor for suitable products is arranged at a front of the machine and the second discharge conveyor for unsuitable products is placed transversely at a lower level than the first discharge conveyor.

5. The device, according claim 1, wherein a set of said retaining elements corresponding with the supporting pads are provided for rotation on a front head of the machine and are located at zones for housing the fruit, each retaining element is activated when the fruit in a position of the respective retaining element has to be rejected, supporting and clamping the fruit to be rejected until it reaches a rejected fruit-discharge position, and not activated when the fruit has to be accepted, allowing it to fall by gravity onto the first discharge conveyor.

6. The device, according to claim 5, wherein the retaining elements are placed in a distribution assembly, each retaining element having a double cam profile determining a dual route including a first interior circular route, when the fruit is accepted, and an exterior variable route, activated by holding clamps when the fruit is rejected.

7. The device, according to claim 6, wherein the retaining elements are made up of an extraction guide whose radial rotation position is fixed, and of an extractable body including holding clamps, whose radial position is variable, with a retracted position in which the clamps do not act on the fruit, and an extended position for supporting and clamping the fruit, and the holding clamps press the fruit from one of outside and laterally against the housing made up of the supporting pads through the effect of a spring.

8. The device, according to claim 7, wherein the holding elements are provided at one end with a hinged portion tending to remain rotated through the effect of the spring in respect of the extractable body when said holding element is located outside the extraction guide, in active position, and forced to remain in an aligned position when said extractable body is inside the extraction guide, in a passive position thereof.

9. The device, according to claim 7, wherein the extractable body of the retainer elements is provided with a lug which constitutes an item following the cam profile of the distribution assembly, and which, depending on the radial position of said lug in the cam profile, determines the extraction or retraction status of the holding clamps.

10. The device, according to claim 9, wherein the cam profile comprises an interior circuit and an exterior circuit, and further comprising a guide pawl activated by an electromechanical item which goes into a closed position, in which the lug of the extractable body travels through an interior, inactive circuit with no radial displacement, and an open position, in which the lug of the extractable body is forced to follow the exterior circuit with radial displacement and opening of the clamps.

11. The device, according to claim 10, wherein the distribution assembly comprises a lower arm which defines a displacement stop of the lug, and one of a slot and groove for re-entry of the lugs into the interior circuit.

12. A method for removing products on the basis of external flaws thereof, comprising the steps of:
   individual transport of the product in housings made up of pairs of supporting pads, and
   separation of one of the products which do not comply with certain parameters by holding said products in their housing by holding clamps during part of outlet travel thereof, preventing the products complying with these parameters from falling by gravity onto a conveyor for collecting the products, and releasing the hold of the products which do not comply with the certain parameters when the product reaches a position of a second conveyor for collecting products which do not comply with those parameters.

13. The device, according to claim 3, wherein the rough, foodstuff-quality material is rubber.

\* \* \* \* \*